United States Patent [19]

McCall

[11] 4,329,459

[45] May 11, 1982

[54] TETRAHYDROBENZOPYRAN DERIVATIVES

[75] Inventor: John M. McCall, Kalamazoo, Mich.

[73] Assignee: The Upjohn Company, Kalamazoo, Mich.

[21] Appl. No.: 146,904

[22] Filed: May 5, 1980

[51] Int. Cl.$^3$ ............................................. C07D 311/04
[52] U.S. Cl. ................................... 544/264; 544/256; 544/236; 544/255; 546/114; 546/115; 546/117; 548/235; 548/336; 548/374; 424/251; 424/270; 424/273 P; 424/274; 424/272; 424/273 R; 548/153; 548/203; 548/407; 548/453; 548/454; 548/525

[58] Field of Search ...................... 544/256, 236, 255; 546/114, 115, 117, 264; 548/153, 374, 203, 336, 235; 260/326.16, 326.5 E, 326.5 D

[56] References Cited

U.S. PATENT DOCUMENTS

| | | | |
|---|---|---|---|
| 3,821,251 | 6/1974 | Fister et al. .......................... | 544/264 |
| 4,080,335 | 1/1978 | Gardner .............................. | 424/244 |
| 4,181,665 | 1/1980 | McCall ............................... | 260/345.2 |
| 4,181,722 | 1/1980 | Bebanger et al. ................... | 260/345.2 |
| 4,200,642 | 4/1980 | Schnur ............................... | 260/345.2 |
| 4,237,162 | 12/1980 | Kabbe et al. ....................... | 260/345.2 |

OTHER PUBLICATIONS

Derwent Farmdoc No. 34290W/21, 2/28/72.
Derwent Farmdoc No. 34291W/21, 2/28/72.
Derwent Farmdoc No. 34318W/21, 2/28/72.
Derwent Farmdoc No. 34319W/21, 2/28/72.
Derwent Farmdoc No. 34320W/21, 2/28/72.

*Primary Examiner*—Nicholas S. Rizzo
*Attorney, Agent, or Firm*—Lawrence T. Welch

[57] ABSTRACT

The present invention provides novel 8-heteroaryltetrahydrobenzopyrans and analogs thereof. These novel compounds are useful as inhibitors of endoperoxide cyclooxygenase which prevents the conversion of unsaturated fatty acids to endoperoxides. Because of this pharmacological activity, these compounds represent potent platelet aggregation inhibitors.

16 Claims, No Drawings

TETRAHYDROBENZOPYRAN DERIVATIVES

DESCRIPTION

Background of the Invention

This invention relates to novel compositions of matter. In particular this invention relates to 8-heteraryltetrahydrobenzopyrans and analogs thereof. Thus this invention relates to benzimidazolyl, imidazopyridine, and similar fused heterocyclic ring substituents on substituted or nonsubstituted benzopyran molecules.

Dihydrobenzopyran has the chemical structure as represented by Formula IV. The positions on the molecule are numbered as shown. The compounds of the present invention have a heterocyclic substituent at the 8 position of the molecule. Further, this invention comprises 8-heteroaryl substituents on benzopyran molecules substituted at the 2 and 5-7 positions of the molecule. The compounds of the present invention will be named herein according to the Chemical Abstracts nunbering system (see Naming and Indexing of Chemical Substances during the Ninth Collective Period (1972-1976), a reprint of Section IV from the Chemical Abstracts Volume 76 Index Guide).

These compounds are endoperoxide cyclooxygenase inhibitors and as such represent potent platelet aggregation inhibitors. They are also useful for one or more other biological purposes commonly associated with cyclooxygenase inhibition, e.g., treatment of asthma and inflamation.

The usefulness of endoperoxide cyclooxygenase inhibitors is well known. (See, e.g. Vane, Nature New Biology, 231-232 (1971) and Vane, Advances in Prostaglandin and Thromboxane Research 4:27 (1978).) Useful cyclooxygenase inhibitors include aspirin, indomethacin, and similar aspirin-like drugs. (See, e.g., Whittle, Acta Obstet Gynecol. Scand. Suppl. 87:21-26 (1979) and Vane, Advances in Prostaglandin and Thromboxane Research 4:27 (1978).)

Prior Art

Imidazopyridine phenyl compounds are known, (see Derwent Farmdoc Nos. 58623V/33, 60978V/34, 45918W/27, and 43447A/24). Benzyl- and benzoyl-imidazopyridine compounds are also known (see Derwent Farmdoc Nos. 34288W/21, 34289W/21, 34290W/21, 34291W/21, 34318W/21, 34319W/21, and 34320W/21). 2-Benzimidazophenol is also known.

The imidazopyridine phenyl compounds are useful as inotropics, having blood pressure lowering and anti-ulcer activity. The benzoyl- and benzyl-imidazopyridine compounds are useful as anti-virals. 2-Benzimidazophenol is manufactured by Aldrich Chemical Company. It is used as a chemical intermediate for a variety of compounds.

SUMMARY OF THE INVENTION

The present invention particularly provides a compound of the formula I, or a pharmaceutically acceptable salt thereof, wherein (a) $R_3$ is hydrogen, halogen, trihalomethyl, alkyl of from one to 8 carbon atoms, or alkoxy of from one to 8 carbon atoms;

(b) $R_5$ is hydrogen, halogen, or alkyl of from one to 8 carbon atoms;

(c) $R_1$ and $R_2$ are the same or different and are hydrogen, alkyl of from one to 3 carbon atoms, or taken together form a spiroalkyl compound of from 3 to 6 carbon atoms;

(d) $R_4$ is selected from the group consisting of heterocycles of the formula II, wherein W is NH, $NR_{10}$, $CH_2$, S, or O;

(e) $R_{10}$ is alkyl of from one to 8 carbon atoms, or aralkyl of 6 to 12 carbon atoms; and (f) $R_8$ and $R_9$ are hydrogen, alkyl of from one to 3 carbon atoms, phenyl or phenyl substituted by one or two of the following:
halogen,
trihalomethyl,
alkyl of from one to 3 carbon atoms,
alkoxy of from one to 3 carbon atoms,
amino or
hydroxy,
or $R_8$ and $R_9$ when taken together with the carbon atoms to which they are attached form a cyclic or heterocyclic moeity selected from the following:
pyridinyl,
pyrimidyl,
phenyl,
pyridazinyl,
pyrazolyl,
triazolyl, and
pyrrolyl,
with the proviso that $R_8$ and $R_9$ form a heterocyclic moiety only when W is not $CH_2$,
said cyclic or heterocyclic moieties are optionally substituted by one or two of the following:
halogen,
trihalomethyl,
alkyl of from one to 3 carbon atoms,
alkoxy of from one to 3 carbon atoms,
amino, or
hydroxy; and the tautomeric forms thereof.

Examples of halogen include fluorine, chlorine, bromine, and iodine. Trihalomethyl includes trifluoromethyl, trichloromethyl, and tribromomethyl. Alkyl includes methyl, ethyl, propyl, butyl, pentyl, hexyl, heptyl, octyl, nonyl, decyl, undecyl, dodecyl, and isomeric forms thereof. Alkoxy includes methoxy, ethoxy, propoxy, butoxy, pentoxy, hexoxy, heptoxy, octoxy, and isomeric forms thereof. Examples of spiroalkyl substituents include cyclopropyl, cyclobutyl, cyclopentyl and cyclohexyl.

Aralkyl includes benzyl, phenethyl, 2-phenylpropyl, 4-phenylbutyl, 6-phenylhexyl, and 5-phenyl-2-methylpentyl.

Examples of substituted heterocyclic moieties include 1-chloropyridyl, 1-fluoropyrimidyl, 3,4-dimethylpyridazinyl, 3-methoxypyrazolyl, 2-amino[1,3,5]triazolyl, 4-hydroxylpyrrolyl, 4-propoxy[1,3,5]triazolo, 3-trichloromethylpyrrolyl, 2,4-diaminopyrimidinyl, and the like.

Pharmaceutically acceptable salts useful for administering the compounds of this invention include hydrochloride, hydrobromide, hydroiodide, sulfate, phosphate, acetate, propionate, lactate, maleate, malate, succinate, tartrate, and the like. These salts may be in hydrated form.

When $R_4$ is an imidazole, the compounds of this invention may exist in one of several tautomeric forms equivalent to the compounds represented herein. The compound may exist in a mixture of the tautomeric forms, the composition of which is dependent on the nature of the other substituents and the chemical environment of the compound.

The novel compounds of this invention are highly active as inhibitors of endoperoxide cyclooxgenase, an enzyme which converts unsaturated fatty acids (e.g., arachidonic acid) to prostaglandin endoperoxide intermediate (e.g., $PGH_2$). The inhibition of this enzyme (also known as PG synthetase) is established in a standard in vitro laboratory test which measures oxygen uptake in the conversion of the unsaturated fatty acid to endoperoxides, as seen in the scheme shown in Chart K. Since this conversion requires oxygen, the inhibition of oxygen uptake is a measure of the inhibition of the enzyme itself. By so measuring the oxygen uptake, the compounds of the present invention have been shown to be potent inhibitors of endoperoxide cyclooxygenase.

For a further description of PG synthetase inhibition, see Vane, Nature New Biology, 231-232 (1971) and Takeguchi, et al., Prostaglandins 2:169 (1972). See also U.S. Pat. No. 4,151,351.

Because of their cyclooxygenase endoperoxide inhibitory activity, the compounds of the present invention are useful as one or more of the following: anti-inflammatory agents, anti-asthma agents, platelet aggregation inhibitors and as agents for treatment of any other disease or condition in mammals which can be treated by blocking this phase of arachidonic acid metabolism.

For example, all of the compounds of the present invention inhibit endoperoxide cyclooxygenase-induced platelet aggregation. Thus, they are useful whenever it is desired to inhibit platelet aggregation, reduce the adhesive character of platelets, and remove or prevent the formation of thrombi in mammals, including man, rabbits, and rats. For example, these compounds are useful in the treatment and prevention of myocardial infarcts, to treat and prevent post-operative thrombosis, to promote patency of vascular grafts following surgery, and to treat conditions such as atherosclerosis, arteriosclerosis, blood clotting defects due to lipemia and other clinical conditions in which the underlying etiology is associated with lipid imbalance or hyperlipidemia. For these purposes, these compounds are administered systemically, e.g., intravenously, orally, subcutaneously, intramuscularly, and in the form of sterile implants for prolonged action. For rapid response, especially in emergency situations, the intravenous route of administration is preferred. Doses in the range of about 0.1 to 10 mg per kg of body weight per day are used, the exact dose depending on the age, weight, and condition of the patient or animal, and on the frequency and route of administration.

These compounds are further useful as additives to blood, blood products, blood substitutes, or other fluids which are used in artificial extracorporeal circulation or perfusion of isolated body portions, e.g., limbs and organs, whether attached to the original body, detached and being preserved or prepared for transplant, or attached to a new body. During these circulation and perfusions, aggregated platelets tend to block the blood vessels and portions of the circulation apparatus. This blocking is avoided by the presence of these compounds. For this purpose, the compound is added gradually or in single or multiple portions to the circulating blood, to the blood of the donor animal, to the perfused body portion, attached or detached, to the recipient, or to two or all of those at a total steady state dose of about 0.005 to 20 mg per liter of circulating fluid. It is especially useful to use these compounds in laboratory animals, e.g., cats, dogs, rabbits, monkeys, and rats, for these purposes in order to develop new methods and techniques for organ and limb transplants.

The compounds of this invention are synthesized as seen in Charts A, B, C and D. In Chart A, an unsubstituted dihydrobenzopyran of the formula X, wherein $R_1$ and $R_2$ are defined as above, is reacted with 2 equivalents of N-halosuccinimide to yield the corresponding dihalo compound of formula XI. This compound is reacted with butyllithium and then carbon dioxide to give the corresponding acid. This acid is then reacted with a diamino aminothio or aminohydroxy compound of the formula III to give the corresponding compound of the formula XIII, wherein $R_1$, $R_2$, $R_3$, $R_5$, $R_8$, and $R_9$ are defined as above; and W is NH, $NR_{10}$, O, or S.

Alternatively, as in Chart B, a benzopyran of the formula XV wherein $R_1$-$R_5$ are defined as above, is reacted with tert-butyllithium and carbon dioxide to give the corresponding acid. This acid is then reacted with an appropriate diamino, amino hydroxy or amino thio compound to yield the corresponding compound of formula XVII, wherein $R_3$ is halogen, $R_5$ is hydrogen, $R_1$, $R_2$, $R_8$ and $R_9$ are defined as above, and W is NH, $NR_{10}$, O or S.

The compounds of the formula I wherein $R_4$ is pyrrole are prepared as seen in Chart C. A compound of the formula XXV is reacted with the Grignard reagent of 3-bromopropionaldehyde ethylene ketal. This adduct is warmed with aqueous oxalic acid, and extracted with methylene chloride. The organic phase is stirred in liquid ammonia to produce the product of formula XXVI. See, e.g., J. Org. Chem., 41,500 (1976) and Synthesis, 281 (1976).

The compounds of formula I where $R_4$ is indole are prepared by reacting a compound of the formula XXX wherein $R_1$, $R_2$, $R_3$ and $R_5$ are defined as above, with phenylhydrazine and then with acid to yield a compound of formula XXXII as seen in Chart D. This process is similar to that disclosed in Review-Heterocyclic Compounds, The Indoles, part 1, pp. 232-316 (1972).

By varying the starting materials e.g., substituted or unsubstituted benzopyran, and amino, diamino, amino hydroxy or amino thio compounds, all the compounds of the present invention may be synthesized using the schemes of Charts A and B. The process of synthesizing the compounds of this invention is seen more fully by the examples given below.

The benzopyran starting materials are prepared according to the schemes given in Charts E to I.

As can be seen, (from Chart E) the 3,4-dihydro-2,2-dialkyl-2H-1-benzopyrans used as the starting material in Chart A are prepared by reacting dihydrocoumarin of formula XXXV with alkylmagnesium bromide and then with hydrochloric acid (or a similar strong acid) to produce a compound of the formula XXXVI. This compound is then reacted with para-toluenesulfonic acid to produce the 3,4-dihydro-2,2-dialkyl-2H-1-benzopyran of the formula XXXVII.

The 2-spiroalkylbenzopyrans are prepared according to Chart F. Dihydrocoumarin (XL) is reacted with alkyldimagnesium bromide (wherein the alkyl portion of the moiety is from 3 to 5 carbon atoms), and then with hydrochloric acid to yield the 2-spiroalkylbenzopyran (XLI).

Substituted benzopyran compunds are formed according to Charts G and H. In Chart G, a 3-, 4- or 5-substituted phenol of the formula XLV is reacted with 2,4-dichloro-2-methyl-butane to yield the corresponding substituted benzopyran (XLV). See Synthesis, 1979, page 126.

Similarly, in Chart H, a phenol of formula L is reacted with 2-methylbutadiene in the presence of aluminum trichloride to yield the corresponding substituted benzopyran (LI). See Angew. Chem. Int. Ed, Vol. 17, page 684 (1978).

Benzopyran starting materials wherein $R_1$ and $R_2$ are different are prepared by the method described in Fieser and Fieser, Reagents for Organic Synthesis, Volume 1, 688 (Wiley and Sons, New York, (1967). This is seen in Chart I. Dihydrocoumarin of the formula LX is reacted with one equivalent of an alkyl lithium in ether. After partitioning the reaction with aqueous ammonium chloride and extracting with ether and drying, the compound is reacted with alkyl magnesium bromide wherein the alkyl group is different than the alkyl lithium group, to yield a compound of formula LXI, wherein $R_1$ and $R_2$ are different.

The benzopyran wherein $R_1$ and $R_2$ are hydrogen, namely 3,4-dihydro-2H-benzopyran, is a well known and readily available compound.

Compounds of the formula IV where W is NH may be converted to compounds wherein W is $NR_{10}$, (wherein $R_{10}$ is defined as above) as can be seen in Chart J. A compound of formula LXV is reacted with sodium hydride and appropriate alkyl halide to produce a compound of formual LXVI.

Preferred compounds of the present invention include those of formula IV wherein $R_3$ is chlorine or hydrogen, $R_5$ is hydrogen, $R_1$ and $R_2$ are methyl, and $R_4$ is benzimidazole, imidazol[4,5-c]pyridine, benzothiazole, 5-chloro-1H-benzimidazole, or 5,6-dimethyl-1H-benzimidazole.

DESCRIPTION OF THE PREFERRED EMBODIMENTS

The present invention is more fully understood by the following examples:

Preparation 1

3,4-Dihydro-2,2-dimethyl-2H-1-benzopyran

Refer to Chart E.

To 475 ml of 2.9 molar methylmagnesium bromide in 1,000 ml of diethyl ether is added dropwise 100 gm (0.675 mols) of dihydrocoumarin in 500 ml of diethyl ether. The reaction is complete after about 2 hr. The mixture is stirred overnight, after which it is cooled in an ice bath. About 20 ml of 1 N hydrochloric acid is carefully added. Concentrated hydrochloric acid is then added and the reaction mixture is extracted with diethyl ether and 10% hydrochloric acid. The organic layer is filtered through sodium sulfate and taken to dryness. The melting point of the crude product is 112°-115° C. This phenol is then taken up in 1500 ml of toluene and heated at reflux overnight with 0.30 gm of p-toluene sulfonic acid under a Dean-Stark trap. The hot toluene is decanted off, leaving behind a small amount of sludge. The toluene solution is extracted with 5% aqueous sodium bicarbonate and brine and the organic layer is filtered through sodium sulfate and taken to dryness. The residue is taken up in methylene chloride and treated with decolorizing carbon. The decolorizing carbon is filtered off and the filtrate is taken to dryness to give 110 gm of liquid product.

Preparation 2

3,4-Dihydro-2,2-tetramethylene-2H-1-benzopyran

Refer to Chart F.

1,4-Dibromobutane (0.05 mole) and Mg turnings (0.1 moles) are heated in ether until the Mg had nearly dissolved. This is added slowly to an ice cold solution of dihydrocoumarin in ether. The mixture is stirred for 3 hr. The ether layer is partitioned with ammonium chloride, brine, and then dried over magnesium sulfate. The organic phase is concentrated, dissolved in methylene chloride, and stirred with 20 mg of p-toluene sulfonic acid for 10 hr. The resultant spiro compound is purified by chromatography on silica gel.

Preparation 3

3,4-Dihydro-2-methyl-2-ethyl-2H-1-benzopyran

Refer to Chart I.

Dihydrocoumarin is reacted with one equivalent of methyl lithium in ether. The reaction is partitioned with aqeuous ammonium chloride and extracted with ether. The ether layer is dried over magnesium sulfate and then reacted with ethyl magnesium bromide. The mixture is partitioned with ammonium chloride and extracted with ether to yield, after drying, concentration, and distillation in vacuo, the 2-methyl-2-ethyl tetrahydropyran.

EXAMPLE 1

2-(3,4-dihydro-2,2-dimethyl-2H-1-benzopyran-8-yl)-1H-benzothiazole

Refer to Chart B.

To 1.4 gm of $P_2O_5$ is added 14 gm of methane sulfonic acid, followed by 1.25 gm (10 mmol) of 2-aminothiophenol and then 2.06 gm (10 mmol) 3,4-dihydro-2,2-dimethyl-8-carboxyl-2H-1-benzopyran. The mixture is stirred at 70° C. for 19 hr. It is then carefully poured into 100 ml of aqueous sodium bicarbonate. The aqueous slurry is then made basic with 50% sodium hydroxide and extracted with $CHCl_2/CHCl_3$. The organic layer is taken to dryness and triturated with diethyl ether ($Et_2O$). The solids are removed and the filtrate is chromatographed on silica gel with 15% ethyl acetate (EtOAc)/Skellysolve B, (a commercial mixture of essentially n-hexane, b.p. 60°-68° C.) (SSB) to give 2.30 gm (78%) of product. The product is crystallized from $CH_2Cl_2/Et_2O$ to give 1.41 gm of product, with a melting point of 127°-128° C.

Anal. Calcd. for $C_{18}H_{17}NOS$: C, 73.18; H, 5.80, N, 4.74. Found: C, 73.01; H, 5.88, N, 4.50.

EXAMPLE 2

2-(3,4-dihydro-2,2-dimethyl-2H-1-benzopyran-8-yl)-1H-benzimidazole

Refer to Chart B.

To 1.4 gm of $P_2O_5$ is added 14 gm of methane sulfonic acid followed by 1.04 gm (9.7 mmol) of o-phenylenediamine and 2.00 gm (9.7 mmol) of 3,4-dihydro-2,2-dimethyl-8-carboxy-2H-1-benzopyran. The mixture is stirred overnight at 60° C., after which it is poured carefully into aqueous sodium bicarbonate. The aqueous slurry is made basic with 15% sodium hydroxide and extracted with $CH_2Cl_2$. The organic layer is taken to dryness and chromatographed on silica gel twice with 2% methanol/$CH_2Cl_2$ to give 0.93 gm (34%). It is crystallized using CH$_2$Cl$_2$/SSB, to give a compound with a melting point of 120°–124° C.

Anal. Calcd. for C$_{18}$H$_{18}$N$_2$O: C, 77.67; H, 6.52; N, 10.07. Found: C, 77.45; H, 6.29; N, 10.12.

EXAMPLE 3

2-(6-chloro-3,4-dihydro-2,2-dimethyl-2H-1-benzopyran-8-yl)-1H-benzimidazole

Refer to Chart A.

To 0.7 gm of P$_2$O$_5$ is added 7.0 gm of methane sulfonic acid. To this is added 4.15 mmol of o-phenylenediamine and then 1.00 gm (4.15 mmol) of 3,4-dihydro-2,2-dimethyl-6-chloro-8-carboxyl-2H-1-benzopyran. The reaction mixture is heated at 70° C. for 19 hr which it is poured onto aqueous sodium bicarbonate and ice. The slurry is made basic with 10% sodium hydroxide and then extracted with CHCl$_3$. The organic layer is taken to dryness and chromatographed on silica gel using 20% EtOAc/SSB. It is recrystallized by triturating with Et$_2$O, to yield 7.81 gm (62%) of a compound having a melting point of 237.5°–238.0° C.

Anal. Calcd. for C$_{18}$H$_{17}$ClN$_2$O: C, 69.31; H, 5.48; N, 8.96. Found: C, 69.02; H, 6.61; N, 9.13.

EXAMPLE 4

2-(6-chloro-3,4-dihydro-2,2-dimethyl-2H-1-benzopyran-8-yl)-5,6-dimethyl-1H-benzimidazole Refer to Chart A.

To 0.7 gm of P$_2$O$_5$ is added 7.0 gm of methane sulfonic acid. To this is added 4.15 mmol of 5,6-dimethyl-o-phenylenediamine and 1.00 gm of 3,4-dihydro-2,2-dimethyl-6-chloro-8-carboxy-2H-1-benzopyran. The reaction mixture is heated at 70° C. for 17 hr after which it is poured onto aqueous sodium carbonate and ice. The slurry is made basic with 10% sodium hydroxide and then is extracted with CHCl$_3$. The organic layer is taken to dryness and chromatographed on silica gel using 20% EtOAc/SSB. The yield is 0.66 gm (47%). The product is then triturated with Et$_2$O, yielding 0.46 gm (33%) of pure product with the melting point of 217.0°–217.5° C.

Anal. Calcd. for C$_{20}$H$_{21}$ClN$_2$O: C, 70.47; H, 6.21; N, 8.22. Found: C, 70.37; H, 6.24; N, 7.91.

EXAMPLE 5

5-chloro-2-(6-chloro-3,4-dihydro-2,2-dimethyl-2H-1-benzopyran-8-yl)-1H-benzimidazole Refer to Chart A.

To 0.7 gm of P$_2$O$_5$ is added 7.0 gm of methane sulfonic acid. To this is added 12.15 mmol of 6-chloro-o-phenylenediamine and then 1.00 gm (4.15 mmol) of 3,4-dihydro-2,2-dimethyl-6-chloro-8-carboxy-2H-1-benzopyran. The reaction mixture is heated at 70° C. for 17–23 hr, after which it is poured onto aqueous sodium carbonate and ice. The slurry is made basic with 7–10% sodium hydroxide and is then extracted with CHCl$_3$. The organic layer is taken to dryness and chromatographed on silica gel, using 6% methanol/CH$_2$Cl$_2$. It is then crystallized from methanol/CH$_2$Cl$_2$/EtOAc/SSB, yielding 1.04 gm (80%) of a product with melting point of 240°–242° C.

Anal. Calcd. for C$_{17}$H$_{16}$ClN$_3$O: C, 65.07; H, 5.14; N, 13.39. Found: C, 65.10; H, 5.00; N, 13.58

EXAMPLE 6

2-(6-chloro-3,4-dihydro-2,2-dimethyl-2H-1-benzopyran-8-yl)-3H-imidazo[4,5-c]pyridine Refer to Chart A.

To 0.7 gm of P$_2$O$_5$ is added 7.0 gm of methane sulfonic acid. To this is added 4.15 mmol of 3,4-pyridinediamine and then 1.00 gm (4.15 mmol) of 3,4-dihydro-2,2-dimethyl-6-chloro-8-carboxyl-2H-1-benzopyran. The reaction mixture is heated at 70° C. for 20 hr, after which it is poured onto aqueous sodium carbonate and ice. The slurry is made basic with 10% sodium hydroxide and is then extracted with CHCl$_3$. The organic layer is taken to dryness and chromatographed on silica gel, using 6% methanol/CH$_2$Cl$_2$. It is then recrystallized from methanol/CH$_2$Cl$_2$/EtOAc/SSB. The yield is 1.04 gm (80%) of crystals with the melting point of 240°–242° C.

Anal. Calcd. for C$_{17}$H$_{16}$ClN$_3$O: C, 65.07; H, 5.14; N, 13.39. Found: C, 65.10; H, 5.00; N, 13.58.

EXAMPLE 7

5,6-dichloro-2(6-chloro-3,4-dihydro-2,2-dimethyl-2H-1-benzopyran-8-yl)-1H-benzimidazole Refer to Chart A.

To 0.7 gm of P$_2$O$_5$ is added 7 gm of methane sulfonic acid. To this is added 4.15 mmol of 1,2-diamino-4,5-dichlorobenzene and then 4.15 mmol of 3,4-dihydro-2,2-dimethyl-6-chloro-8-carboxyl-2H-1-benzopyran. The reaction mixture is heated at 70°–80° C. for 18 hr, after which it is poured onto aqeuous sodium carbonate and ice. The slurry is then extracted with methylene chloride. The organic layer is then dried over Na$_2$SO$_4$ and chromatographed on silica gel using 2% methanol/CH$_2$Cl$_2$. The product is then crystallized from the solution, yielding 1.37 gm (86%) of crystals with the melting point of 230.0°–230.5° C.

Anal. Calcd. for C$_{18}$H$_{15}$Cl$_3$N$_2$O: C, 56.64; H, 3.96; N, 7.34. Found: C, 56.24; H, 3.96; N, 7.39.

EXAMPLE 8

8-(6-chloro-3,4-dihydro-2,2-dimethyl-2H-1-benzopyran-8-yl)-7H-purine

Refer to Chart A.

To 0.7 gm of P$_2$O$_5$ is added 7 gm of methane sulfonic acid. To this is added 4.15 mmol of 4,5-diaminopyrimidine and 4.15 mmol of 3,4-dihydro-2,2-dimethyl-6-chloro-8-carboxyl-2H-1-benzopyran. The reaction mixture is heated at 70°–80° C. for 46.5 hr after which it is poured onto aqueous sodium bicarbonate and ice. The slurry is extracted with methylene chloride. The organic layer is then dried over Na$_2$SO$_4$ and chromatographed on silica gel, using 4% methanol/CH$_2$Cl$_2$ as eluent. The product is recrystallized from ethanol/CH$_2$Cl$_2$. The yield is 0.84 gm (64%) of crystals with a melting point of 264.5°–265.0° C.

Anal. Calcd. for C$_{16}$H$_{15}$ClN$_4$O: C, 61.05; H, 4.80; N, 17.80. Found: C, 60.80; H, 4.77; N, 17.95.

EXAMPLE 9

2-(3,4-dihydro-2,2-dimethyl-2H-1-benzopyran-8-yl)-3H-imidazol[4,5-c]pyridine

Refer to Chart B.

To 0.7 gm of P$_2$O$_5$ is added 7 gm of methane sulfonic acid. To this is added 4.15 mmol of 3,4-diaminopyridine and then 4.15 mmol of 3,4-dihydro-2,2-dimethyl-6- chloro-8-carboxyl-2H-1-benzopyran. The reaction mixture is heated at 70°–80° C. for 21 hr after which it is poured onto aqueous sodium carbonate and ice. The slurry is extracted with methylene chloride. The organic layer is dried over $Na_2SO_4$ and chromatographed on silica gel, using 4% methanol/$CH_3Cl_2$ as an eluent. The product is recrystallized from methanol/$CH_2Cl_2$/SSB. The yield is 1.20 gm (89%) of crystals with a melting point of 176°–177° C.

Anal. Calcd. for $C_{17}H_{17}N_3O$: C, 73.09; H, 6.14; N, 15.04. Found: C, 73.04; H, 6.40; N, 14.96.

EXAMPLE 10

2-(6-chloro-3,4-dihydro-2,2-dimethyl-2H-1-benzopyran-8-yl)-benzothiazole

Refer to Chart A.

To 0.7 gm of $P_2O_5$ is added 7 gm of methane sulfonic acid. To this is added 4.15 mmol of 1-amino-2-thiobenzene and then 4.15 mmol of 3,4-dihydro-2,2-dimethyl-6-chloro-8-caboxyl-2H-1-benzopyran. The reaction mixture is heated at 70°–80° C. for 21.5 hr after which it is poured onto aqueous sodium carbonate and ice. This slurry is extracted with methylene chloride. The organic layer is dried over $Na_2SO_4$ and chromatographed on silica gel, using 10% ethyl acetate/SSB as eluent. The product is recrystallized, yielding 2.88 gm of product of melting point 146°–147° C.

Anal. Calcd. for $C_{18}H_{16}ClNO_S$: C, 65.54; H, 4.89; N, 4.25. Found: C, 65.38; H, 4.80; N, 4.12.

EXAMPLE 11

6-(3,4-Dihydro-2,2-dimethyl-2H-1-benzopyran-8-yl)-5H-Imidazo[4,5-c]pyridazine

Refer to Chart B.

To 1.4 gm of $P_2O_5$ is added 14 gm of methanesulfonic acid followed by 10 mmol of 3,4-diamopyridazine and 10 mmol of 3,4-dihydro-2,2-dimethyl-8-carboxyl-2H-1-benzopyran. The mixture is stirred at 70° C. for 19 hr after which it is carefully poured into 100 ml of aqueous sodium bicarbonate. The aqueous slurry is then made basic with 50% sodium hydroxide and then extracted with $CH_2Cl_2$/$CHCl_3$. The organic layer is taken to dryness and triturated with diethyl ether. The solids are removed and the filtrate is chromatographed on silica gel with 15% EtOAc/SSB, after which it is crystallized from $CH_2Cl_2$/EtO to yield the product.

EXAMPLE 12

2-(6-Chloro-3,4-dihydro-2,2-dimethyl-2H-1-benzopyran-8-yl)-1H-imidazo[4,5-b]pyrazine Refer to Chart A.

To 0.7 gm of $P_2O_5$ is added 7.0 gm of methanesulfonic acid to this is added 4.15 mmol of 2,3-diaminopyrazine and then 1.00 gm (4.15 mmol) of 8-carobxyl-6-chloro-3,4-dihydro-2,2-dimethyl-2H-1-benzopyran. The reaction mixture is treated at 70° C. for 19 hr after which it is poured onto aqueous sodium bicarbonate and ice. The slurry is made basic with 10% sodium hydroxide and then extracted with $CHCl_3$. The organic layer is taken to dryness and chromatographed on silica gel using 20% EtOAc/SSB. It is recrystallized by triturating with $Et_2O$, to yield the product.

EXAMPLE 13

6-(3,4-Dihydro-2,2-dimethyl-2H-1-benzopyran-8-yl)-5H-imidazo[4,5-e],[1,2,4]triazine Refer to Chart B.

To 1.4 gm of $P_2O_5$ is added 14 gm of methanesulfonic acid followed by 9.7 mmol of 5,6-diamino[1,2,4]triazine and 200 gm (9.7 mmol) of 8-carboxy-3,4-dihydro-2,2-dimethyl-2H-1-benzopyran. The mixture is stirred overnight at 60° C., after which it is poured carefully into aqueous sodium bicarbonate. The aqueous slurry is made basic with 15% sodium hydroxide and extracted with $CH_2Cl_2$. The organic layer is taken to dryness and chromatographed on silica gel twice with 2% methanol/$CH_2Cl_2$ and crystallized from $CH_2Cl_2$/SSB to yield the product.

EXAMPLE 14

2-(6-Chloro-3,4-dihydro-2,2-dimethyl-2H-1-benzopyran-8-yl)-1,4-dihydropyrrolo[2,3]imidazole Refer to Chart B.

To 0.7 gm of $P_2O_5$ is added 7.0 gm of methanesulfonic acid. To this is added 4.15 mmol of 2,3-diaminopyrrole and then 1.00 gm (4.15 mmol) of 8-carboxyl-6-chloro-3,4-dichloro-2,2-dimethyl-2H-1-benzopyran. The reaction mixture is heated at 70° C. for 19 hr after which it is poured onto aqueous sodium bicarbonate and ice. The slurry is made basic with 10% sodium hydroxide and then extracted with $CHCl_3$. The organic layer is taken to dryness and chromatographed on silica gel using 20% EtOAc/SSB. It is triturated with $Et_2O$, yielding the product.

EXAMPLE 15

2-(3,4-Dihydro-2,2-dimethyl-2H-1-benzopyran-8-yl)-1H-benzoxazole

Refer to Chart B.

To 1.4 gm of $P_2O_5$ is added 14 gm of methanesulfonic acid followed by 9.7 mmol of 2-aminophenol and 2.00 gm (9.7 mmol) of 8-carboxyl-3,4-dihydro-2,2-dimethyl-2H-1-benzopyran. The mixture is stirred overnight at 60° C., after which it is poured carefully into aqueous sodium bicarbonate. The aqueous slurry is made basic with 15% sodium hydroxide and extracted with $CH_2Cl_2$. The organic layer is taken to dryness and chromatographed on silica gel with 2% methanol/$CH_2Cl_2$ and crystallized from $CH_2Cl_2$/SSB to yield the product.

EXAMPLE 16

2-(6-Chloro-3,4-dihydro-2,2-dimethyl-2H-1-benzopyran-8-yl)-5-benzyl-1H-benzimidazole Refer to Chart A.

To 0.7 of $P_2O_5$ is added 7 gm of methanesulfonic acid. To this is added 4.15 mmol of 1-benzyl-3,4-diaminobenzene and then 4.15 mmol of 3,4-dihydro-2,2-dimethyl-6-chloro-8-carboxyl-2H-1-benzopyran. The reaction mixture is heated at 70°–80° C. for 20 hr after which it is poured onto aqueous sodium carbonate and ice. The slurry is extracted with methylene chloride. The organic layer is dried over $Na_2SO_4$ and chromatographed on silica gel, using 4% methanol/$CH_2Cl_2$ as an eluant. The product is recrystallized from methanol/$CH_2Cl_2$/SSB to yield the title product.

EXAMPLE 17

2-(6-Chloro-3,4-dihydro-2,2-dimethyl-2H-1-benzopyran-8-yl)-4,5-dihydro-4-ethyl-1H-imidazole Refer to Chart A.

To 0.7 gm of $P_2O_5$ is added 7 gm of methanesulfonic acid to this is added 4.15 mmol of 1,2-diaminobutane and 4.15 mmol of 8-carboxyl-6-chloro-3,4-dihydro-2,2-dimethyl-2H-1-benzopyran. The reaction mixture is heated at 70°–80° C. for 20 hr after which it is poured into aqueous sodium carbonate and ice. The slurry is extracted with methylene chloride. The organic layer is dried over $Na_2SO_4$ and chromatographed on silica gel, using 4% methanol/$CH_2Cl_2$ as an eluant. The product is recrystallized from methanol/$CH_2Cl_2$/SSB to yield the title product.

EXAMPLE 18

2-(6-Chloro-3,4-dihydro-2,2-dimethyl-2H-1-benzopyran-8-yl)-1H-imidazo[4,5-b]pyridine monohydrochloride Refer to Chart A.

A mixture of 2.50 g (0.0104 mole) of the 8-carboxy-6-chloro-3,4-dihydro-2,2-dimethyl-2H-1-benzopyran, 1.13 g (0.0104 mole) of 2,3-diaminopyridine, 1.5 g of $P_2O_5$, and 15 g of methanesulfonic acid is heated at 70° C. for 70 hrs. The mixture is then poured onto 10% NaOH/ice and is extracted with $CH_2Cl_2$. The organic layer is taken to dryness ($Na_2SO_4$) and the residue is chromatographed (4% MeOH/$CH_2Cl_2$), on silica gel to give 1.63 g (50%) of product. Crystallization from $CH_2Cl_2$/MeOH gave 1.38 g of product, m.p. 270–271. The hydrochloride salt is prepared with HCl/EtOH and was crystallized from EtOH to give 1.10 g of the salt, m.p. 244–253.

Anal. Calcd. for $C_{17}H_{16}ClN_3O \cdot HCl$: C, 58.29; H, 4.89; N, 12.00; Cl, 20.02. Found: C, 58.29; H, 4.80; N, 12.08; Cl, 19.80.

EXAMPLE 19

2-(6-Chloro-3,4-dihydro-2,2-dimethyl-2H-1-benzopyran-8-yl)-1-phenyl(1H)-benzimidazole Refer to Chart A.

A mixture of 1.50 g (0.00623 mole) of the 8-carboxy-6-chloro-3,4-dihydro-2,2-dimethyl-2H-1-benzopyran, 1.18 g (0.00623 mole) of N-phenyl-o-phenylenediamine, 1.0 g of $P_2O_5$, and 10 g of methanesulfonic acid is heated at 70° C. for 19 hrs, after which it is poured onto 10% NaOH and ice. The mixture is extracted with $CH_2Cl_2$ and taken to dryness ($Na_2SO_4$). The residue is chromatographed (½% MeOH/$CH_2Cl_2$) to give 0.51 g (21%) of product, m.p. 155–156.

Anal. Calcd. for $C_{24}H_{21}ClN_2O$: C, 74.12; H, 5.44; N, 7.20. Found: C, 73.64; H, 5.40; N, 7.16.

EXAMPLE 20

2-(6-Chloro-2,2-dimethyl-2H-1-benzopyran-8-yl)-1-methyl-1H-benzimidazole

Refer to Chart J.

A mixture of 1.0 g (0.0032 mole) of the compound of Example 2 in 1,2-dimethoxyethane is added to 0.0032 mole of sodium hydride. After stirring for 1.5 hrs, 0.22 ml (0.0035 mole) of methyl iodide is added. The mixture is stirred for one hour, after which the solvent is removed in vacuo. The residue is extracted with $CH_2Cl_2$ and brine. The organic layer is taken to dryness ($Na_2SO_4$) and the residue is chromatographed (25% EtOAc/SSB) on silica gel. Crystallization from $Et_2O$/SSB gives 0.85 g (82%) of product, m.p. 153°–154° C.

Anal. Calcd. for $C_{19}H_{19}N_2Cl$: C, 69.82; H, 5.86; N, 8.57. Found: C, 70.06; H, 5.86; N, 8.65.

EXAMPLE 21

2-(3,4-dihydro-2,2-dimethyl)-2H-benzopyran-8-yl)indole

Refer to Chart D.

8-Aceto-3,4-dihydro-2,2-dimethyl-2H-1-benzopyran (0.05 mol) and phenyl hydrazine (0.05 mol) are stirred with 10 mg of p-toluenesulfonic acid in 50 ml of ethanol. After 8 hr, the mixture is concentrated and the phenyl hydrazone product is crystallized from ether. This is refluxed in 20 ml of ethanol with 5 ml of trifluoroacetic acid for 8 hr. The mixture is concentrated and the resultant indole is purified by chromatography on silica gel. The column is eluted with methanol and methylene chloride to yield the product which is crystallized from methylene chloride/SSB.

EXAMPLE 22

Following the procedures of the preceding examples the following compounds are synthesized:

2-(3,4-dihydro-2,2-dimethyl-2H-1-benzopyran-8-yl)-1H-imidazo[4,5-c]pyridine, 2-(3,4-dihydro-2,2-spirocyclopropyl-2H-1-benzopyran-8-yl)-1H-imidazo[4,5-c]pyridine, 2-(2,2-diethyl-3,4-dihydro-2H-1-benzopyran-8-yl)-1H-imidazo-[4,5-c]pyridine, 2-(3,4-dihydro-2,2-dipropyl-2H-1-benzopyran-8-yl)-1H-imidazo[4,5-c]pyridine, 2-(5-chloro-3,4-dihydro-2,2-dimethyl-2H-1-benzopyran-8-yl)-1H-benzimidazole, 6-(3,4-dihydro-2,2-dimethyl-2H-1-benzopyran-8-yl)-5H-imidazo[4,5-e][1,2,4]triazine, 2-(3,4-dihydro-2,2-dimethyl-2H-1-benzopyran-8-yl)-4-methyl-1,4-dihydropyrrolo[2,3-d]imidazole, 2-(3,4-dihydro-2,2-dimethyl-2H-1-benzopyran-8-yl)-1-octyl-1H-benzimidazole, 1-benzyl-2-(3,4-dihydro-2,2-dimethyl-2H-1-benzopyran-8-yl)-1H-imidazo[4,5-c]pyridine, 2-(3,4-dihydro-2,2-dimethyl-6-trifluoromethyl-2H-1-benzopyran-8-yl)-1,4-dihydropyrrolo[2,3-d]imidazole, 6-(3,4-dihydro-2,2-dimethyl-6-hexyl-2H-1-benzopyran-8-yl)-5H-imidazolo[4,5-e][1,2,4]triazine, 2-(3,4-dihydro-2,2-dimethyl-6-methyl-2H-1-benzopyran-8-yl)indole, 2-(7-chloro-3,4-dihydro-2,2-dimethyl-2H-1-benzopyran-8-yl)-1H-benzoimidazole, 2-(6-propoxy-3,4-dihydro-2,2-dimethyl-2H-1-benzopyran-8-yl)-benzimidazole, 2-(6-chloro-3,4-dihydro-2,2-dimethyl-7-methyl-2H-1-benzopyran-8-yl)-1H-benzimidazole, 2-(6-chloro-3,4-dihydro-2,2-dimethyl-2H-1-benzopyran-8-yl)-4,5-dihydro-4-phenyl-1H-imidazole, 2-(6-chloro-3,4-dihydro-2,2-dimethyl-2H-1-benzopyran-8-yl)-4,5-dihydro-4,5-dimethyl-1H-imidazole, 2-(6-chloro-3,4-dihydro-2,2-dimethyl-2H-1-benzopyran-8-yl)-4-(4-methylphenyl)pyrrole.

All of the other compounds of this invention are also synthesized by these means.

FORMULAS
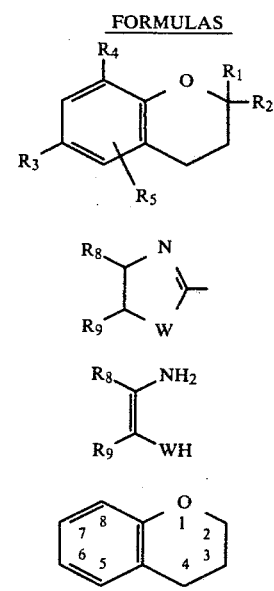
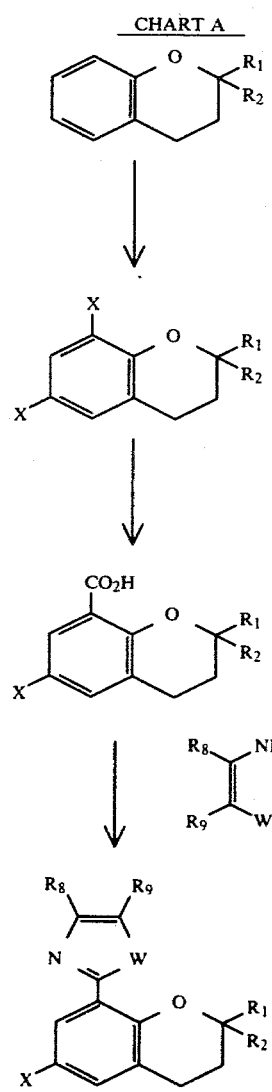
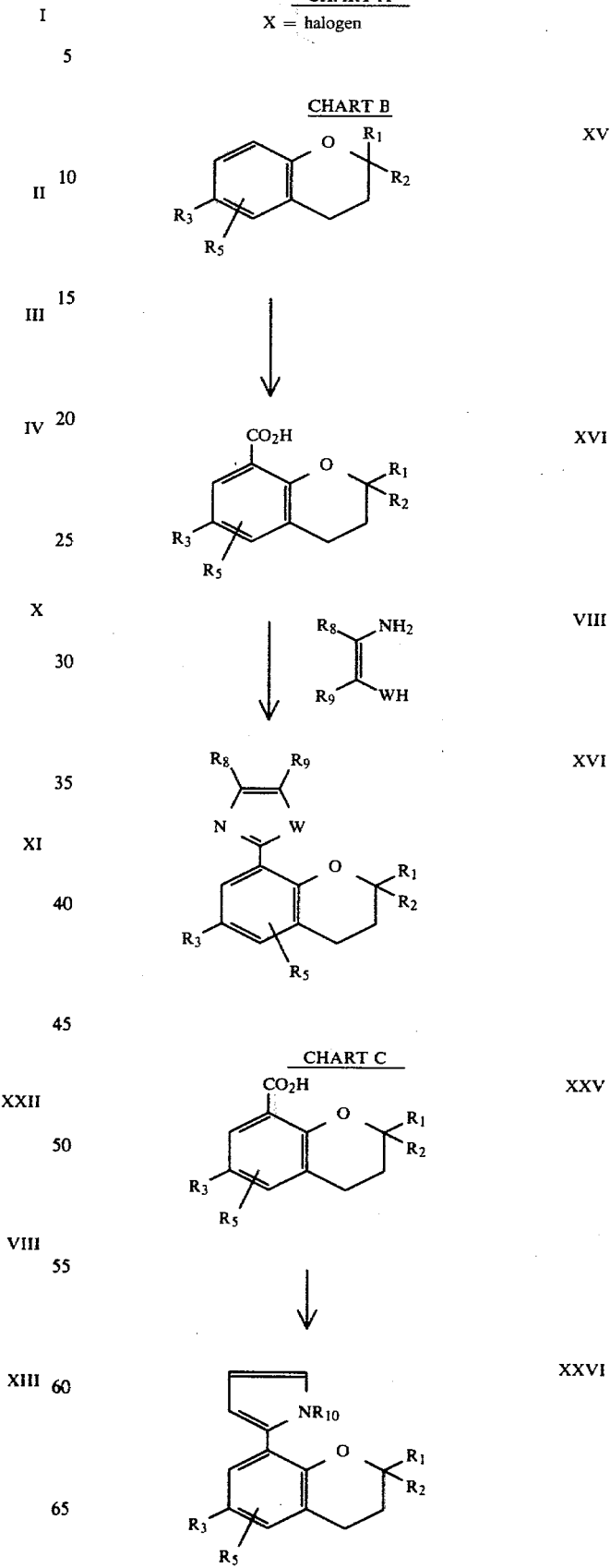

CHART D
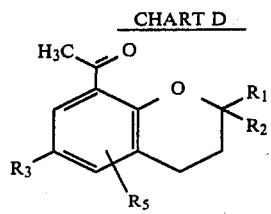
XXX
↓
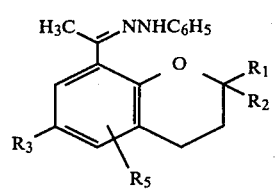
XXXI
↓ H+
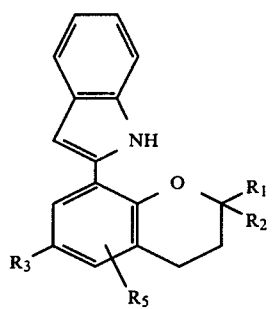
XXXII
CHART E
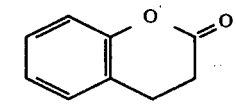
XXXV
↓
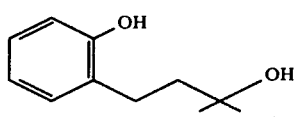
XXXVI
↓
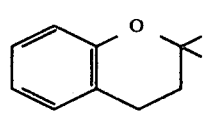
XXXVII
CHART F
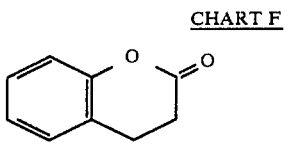
XL
↓ BrMg—(CH₂)ₙ—CH₂CH₂—MgBr
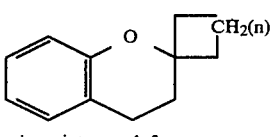
XLI
n is an interger 1–3
CHART G
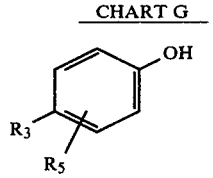
XLV
+
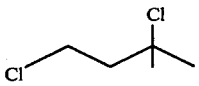
↓
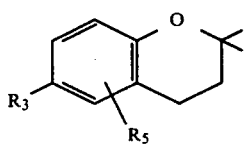
XLVI
CHART H
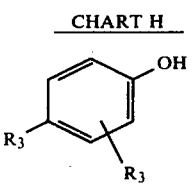
L
+
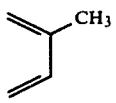
↓

-continued
CHART H

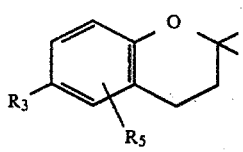

CHART I

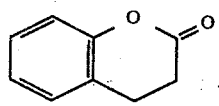

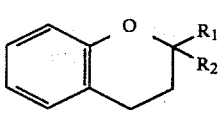

CHART J

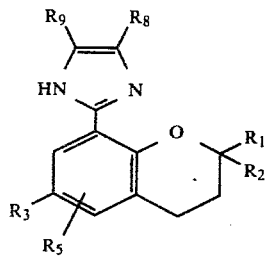

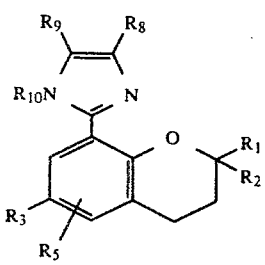

CHART K

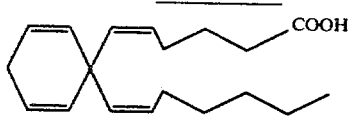

-continued
CHART K

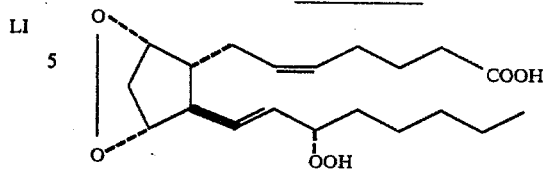    LXXI

I claim:
1. A compound of the formula I

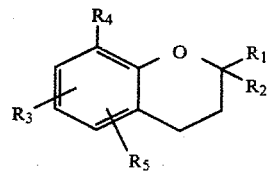    I or a pharmaceutically acceptable salt thereof, wherein
(a) $R_3$ is hydrogen, halogen, trihalomethyl, alkyl of from one to 8 carbon atoms, or alkoxy of from one to 8 carbon atoms;
(b) $R_5$ is hydrogen, halogen, alkyl of from one to 8 carbon atoms;
(c) $R_1$ and $R_2$ are the same or different and are hydrogen, alkyl of from one to 3 carbon atoms, or taken together form a spiroalkyl compound of from 3 to 6 carbon atoms;
(d) $R_4$ is selected from the group consisting of heterocycles of formula II;

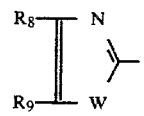    II wherein W is NH, $NR_{10}$, $CH_2$, S, OR O;
(e) $R_{10}$ is hydrogen, alkyl of from one to 8 carbon atoms, or aralkyl of from 6 to 12 carbon atoms; and
(f) $R_8$ and $R_9$ are hydrogen, alkyl of from one to 3 carbon atoms, phenyl or phenyl substituted by one or two of the following:
halogen,
trihalomethyl,
alkyl of from one to 3 carbon atoms,
alkoxy of from one to 3 carbon atoms,
amino, or
hydroxy,
of from 3 to 8 carbon atoms,
or when taken together with the carbon atoms to which they are attached form a cyclic or heterocyclic moiety selected from the following:
pyridyl,
pyrimidyl,
phenyl,
pyridazinyl,
pyrazolyl,
triazolyl, and
pyrrolyl,
with the proviso that $R_8$ and $R_9$ form a heterocyclic moiety only when W is not $CH_2$,
said cyclic heterocyclic moieties are optionally substituted by one or two of the following:
halogen, trihalomethyl,
alkyl of from one to 3 carbon atoms,
alkoxy of from one to 3 carbon atoms,
amino, or hydroxy;
and the tautomeric forms thereof.

2. 8-(6-Chloro-3,4-dihydro-2,2-dimethyl-2H-1-benzopyran-8-yl)-7H-purine, a compound of claim 1.

3. 2-(6-Chloro-3,4-dihydro-2,2-dimethyl-2H-1-benzopyran-8-yl)-1H-imidazo[4,5-b]pyridine monohydrochloride, a compound of claim 1.

4. 2-(6-Chloro-3,4-dihydro-2,2-dimethyl-2H-1-benzopyran-8-yl)-1-phenyl(1H)-benzimidazole, a compound of claim 1.

5. 2-(6-Chloro-2,2-dimethyl-2H-1-benzopyran-8-yl)-1-methyl-1H-benzimidazole, a compound of claim 1.

6. A compound of claim 1 wherein $R_3$ is chlorine or hydrogen, $R_5$ is hydrogen, $R_4$ is benzimidazolyl, 3H-imidazo[4,5-c]pyridine, benzothiazole, 6-chlorobenzimidazole, or 5,6-dimethylbenzimidazole, and $R_1$ and $R_2$ are methyl.

7. 2-(3,4-Dihydro-2,2-dimethyl-2H-1-benzopyran-8-yl)-1H-benzothiozole, a compound of claim 6.

8. A compound of claim 2 wherein $R_4$ is benzimidazole.

9. 2-(3,4-Dihydro-2,2-dimethyl-2H-1-benzopyran-8-yl)-1H-benzimidazole, a compound of claim 8.

10. 2-(6-Chloro-3,4-dihydro-2,2-dimethyl-2H-1-benzopyran-8-yl)-1H-benzimidazole, a compound of claim 8.

11. 2-(6-Chloro-3,4-dihydro-2,2-dimethyl-2H-1-benzopyran-8-yl)-5,6-dimethyl-1H-benzimidazole, a compound of claim 8.

12. 5-Chloro-2-(6-chloro-3,4-dihydro-2,2-dimethyl-2H-1-benzopyran-8-yl)-1H-benzimidazole, a compound of claim 8.

13. 5,6-Dichloro-2-(6-chloro-3,4-dihydro-2,2-dimethyl-2H-1-benzopyran-8-yl)-1H-benzimidazole, a compound of claim 8.

14. A compound of claim 2 wherein $R_4$ is 3H-imidazo[4,5-c]-pyridine.

15. 2-(6-Chloro-3,4-dihydro-2,2-dimethyl-2H-1-benzopyran-8-yl)-3H-imidazo[4,5-c]pyridine, a compound of claim 14.

16. 2-(3,4-Dihydro-2,2-dimethyl-2H-1-benzopyran-8-yl)-3H-imidazol[4,5-c]pyridine, a compound of claim 14.

* * * * *

UNITED STATES PATENT OFFICE
CERTIFICATE OF CORRECTION

Patent No. 4,329,459   Dated 11 May 1982

Inventor(s)  John M. McCall

It is certified that error appears in the above-identified patent and that said Letters Patent are hereby corrected as shown below:

Column 10, line 9, "200 gm" should read -- 2.00 gm --.
Column 10, line 21, "[2,3]imidazole" should read -- [2,3-d]imidazole --.
Column 16, line 55, the portion of that formula should appear as
   follows:

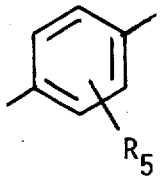

Signed and Sealed this

Twenty-eighth Day of December 1982

[SEAL]

Attest:

GERALD J. MOSSINGHOFF

Attesting Officer

Commissioner of Patents and Trademarks